(12) United States Patent
Bilic et al.

(10) Patent No.: US 9,103,705 B2
(45) Date of Patent: Aug. 11, 2015

(54) COMBINED ENVIRONMENTAL PARAMETER SENSOR

(75) Inventors: Dubravka Bilic, Scottsdale, AZ (US); Andrew C. McNeil, Chandler, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 396 days.

(21) Appl. No.: 13/406,439

(22) Filed: Feb. 27, 2012

(65) Prior Publication Data
US 2013/0219994 A1 Aug. 29, 2013

(51) Int. Cl.
*G01N 7/00* (2006.01)
*G01D 21/02* (2006.01)
*G01D 1/00* (2006.01)
*G01L 19/14* (2006.01)
*G01L 11/02* (2006.01)
*G01N 19/10* (2006.01)
*G01L 19/00* (2006.01)

(52) U.S. Cl.
CPC .................. *G01D 21/02* (2013.01); *G01D 1/00* (2013.01); *G01L 11/025* (2013.01); *G01L 19/14* (2013.01); *G01L 2019/0053* (2013.01); *G01N 19/10* (2013.01)

(58) Field of Classification Search
CPC ..... G01L 19/0092; G01L 11/04; G01L 19/04; G01D 21/02
USPC .......................................................... 73/754
See application file for complete search history.

(56) References Cited

U.S. PATENT DOCUMENTS

| | | |
|---|---|---|
| 5,048,336 A | 9/1991 | Sugihara et al. |
| 5,388,443 A * | 2/1995 | Manaka ........................ 73/31.06 |
| 5,563,341 A | 10/1996 | Fenner et al. |
| 7,340,941 B1 | 3/2008 | Fruhberger et al. |
| 7,523,643 B2 | 4/2009 | Chen et al. |
| 7,556,775 B2 | 7/2009 | McGill et al. |
| 7,640,798 B2 * | 1/2010 | Oda ............................ 73/204.26 |
| 7,793,550 B2 * | 9/2010 | Elian et al. ....................... 73/754 |
| 7,832,269 B2 * | 11/2010 | Bey et al. ......................... 73/431 |
| 8,476,084 B1 * | 7/2013 | Yang et al. ......................... 438/3 |
| 8,477,473 B1 * | 7/2013 | Koury, Jr. et al. .............. 361/287 |
| 2007/0295084 A1 * | 12/2007 | Chang et al. ................ 73/335.02 |
| 2009/0288484 A1 * | 11/2009 | Selvan et al. ............... 73/335.02 |
| 2011/0132096 A1 * | 6/2011 | Ricks ............................... 73/708 |
| 2011/0146382 A1 * | 6/2011 | Fleischer et al. ............. 73/25.01 |
| 2011/0265574 A1 * | 11/2011 | Yang ................................. 73/658 |
| 2012/0240674 A1 * | 9/2012 | Sakuma ..................... 73/204.25 |
| 2013/0055821 A1 * | 3/2013 | Bentley et al. .................. 73/721 |

OTHER PUBLICATIONS

Hautefeuille, Mathieu, et al. "Development of a microelectromechanical system (MEMS)-based multisensor platform for environmental monitoring."Micromachines 2.4 (2011): 410-430.*

Won, Jonghwa, Sung-Hoon Choa, and Zhao Yulong. "An integrated sensor for pressure, temperature, and relative humidity based on MEMS technology."Journal of mechanical science and technology 20.4 (2006): 505-512.*

* cited by examiner

*Primary Examiner* — Lisa Caputo
*Assistant Examiner* — Punam Roy

(57) ABSTRACT

A combination sensor and corresponding method of measuring a plurality of environmental parameters uses a pressure sensor disposed on an integrated circuit die; a humidity sensor disposed on the integrated circuit die; and a circuit coupled to and shared by the pressure sensor and the humidity sensor to facilitate pressure and humidity sensing.

14 Claims, 3 Drawing Sheets

COMBINED ENVIRONMENTAL PARAMETER SENSOR

FIELD OF THE INVENTION

This invention relates in general to sensors and more specifically to techniques and apparatus for combining various environmental parameter sensors.

BACKGROUND OF THE INVENTION

In some applications it can be advantageous if more than one environmental parameter is known or can be estimated. For example in hard disk drives, humidity and pressure within the environment, if known, can be used to better position read/write heads and thereby reliably increase data density for the hard disk drive.

Sensors for various environmental parameters are known. For example, temperature sensors are known as well as environmental humidity and pressure sensors. Additionally various approaches, e.g., cantilever beams, etc., for sensing different parameters are available. Additionally different issues concern different sensors or have differing impacts on one type of sensor versus another. E.g., a temperature measurement may have to account for the present humidity depending on the sensing structure that is used.

BRIEF DESCRIPTION OF THE DRAWINGS

The accompanying figures where like reference numerals refer to identical or functionally similar elements throughout the separate views, wherein the various structures and features are not necessarily drawn to scale, and which together with the detailed description below are incorporated in and form part of the specification, serve to further illustrate various embodiments and to explain various principles and advantages all in accordance with the present invention.

DETAILED DESCRIPTION

In various embodiments, the present disclosure concerns sensing environmental parameters, e.g., pressure, humidity, temperature and the like, and more specifically techniques and apparatus that are arranged and constructed for sensing or to sense more than one parameter. More particularly various inventive concepts and principles embodied in methods and apparatus, e.g. combination sensors arranged and constructed to sense or measure a plurality of parameters will be discussed and disclosed.

The sensors and methods of particular interest may vary widely but include pressure and humidity sensors that can be advantageously configured in combination. In systems, equipment and devices that can employ more than one measurement of environmental parameters or multiple sensors, e.g., hard disk drives, etc., the combination apparatus and methods can be particularly advantageously utilized, provided they are practiced in accordance with the inventive concepts and principles as taught herein.

The instant disclosure is provided to further explain in an enabling fashion the best modes, at the time of the application, of making and using various embodiments in accordance with the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms, if any, such as first and second, and the like are used solely to distinguish one from another entity or action without necessarily requiring or implying any actual such relationship or order between such entities or actions.

Much of the inventive functionality and many of the inventive principles are best implemented with or in integrated circuit processes and integrated circuits (ICs) including possibly application specific ICs or ICs with integrated processing controlled by embedded software or firmware. It is expected that one of ordinary skill, notwithstanding possibly significant effort and many design choices motivated by, for example, available time, current technology, and economic considerations, when guided by the concepts and principles disclosed herein will be readily capable of using the integrated circuit processes and generating ICs and any software instructions and programs and with minimal experimentation. Therefore, in the interest of brevity and minimization of any risk of obscuring the principles and concepts according to the present invention, further discussion of such processes, ICs, and software, if any, will be limited to the essentials with respect to the principles and concepts of the various embodiments.

Figure 1:
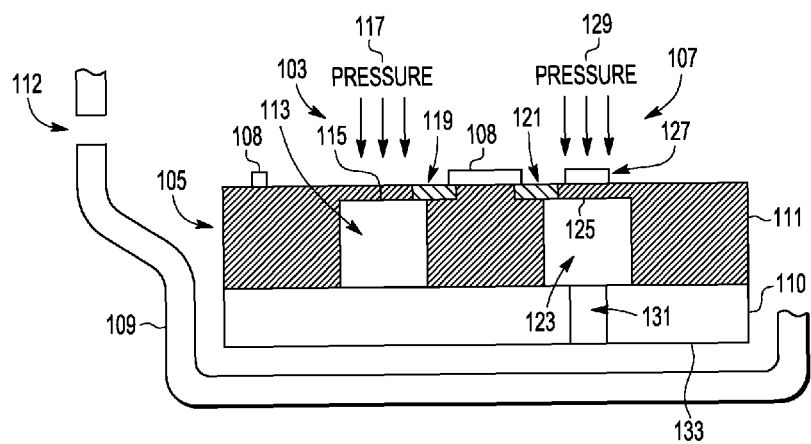
FIG. 1 depicts in a simplified and representative form, a cross sectional side view diagram of a combination sensor in accordance with one or more embodiments.

Referring to FIG. 1, a simplified and representative cross sectional side view diagram of a combination sensor in accordance with one or more embodiments will be briefly discussed and described. In FIG. 1, a side view of a combination sensor 101 is illustrated where this combination sensor is one of a family of devices that is known in the industry as a MEMS (Micro ElectroMechanical Systems), where some mechanical properties of Silicon or other structures are utilized often together with some integrated electronics to provide or perform some useful function. The combination sensor in many embodiments and as illustrated includes a pressure sensor 103 disposed on a carrier or a die 105 comprised of a semiconductor material or an integrated circuit die 105. Further included is a humidity sensor 107 disposed on the same carrier or integrated circuit die 105. Additionally, included, but shown only in part in FIG. 1, is a circuit 108 coupled to and shared by the pressure sensor and the humidity sensor to facilitate pressure and humidity sensing. This circuit including, e.g., traces, bonding pads, etc., can be disposed on the top or near top surface of the integrated circuit die 105 and will be further shown and discussed with reference to FIG. 2 and FIG. 4. Further included in many embodiments, is a sensor package 109 (shown in part and in representative fashion) that is arranged and constructed for encasing the pressure sensor and humidity sensor and possibly other functions, wherein a common port or opening 112 to provide access to the outside environment for both sensors is further included. Appropriate packaging techniques will be evident to those of ordinary skill and may vary with particular applications of the combination sensor.

The integrated circuit die in some embodiments typically includes a base or carrier wafer 110 and then a top or an upper layer 111. It will be appreciated that these are not shown to scale as the carrier wafer can be much thicker than the upper or top layer 111. The carrier wafer is typically silicon, e.g., a silicon wafer, or some other material that can be suitable for the purpose (ceramic, etc.). Generally the top layer is also silicon and can be processed separately from and later bonded to the carrier wafer.

The pressure sensor 103 is generally comprised of a cavity 113, which may be referred to as a pressure reference cavity. Further included is a diaphragm 115 which is a thin layer (typically silicon layer of 6 microns or so). This reference cavity 113 can be formed in the upper or top layer 111 via a directional or anisotropic etch from the back side with the etch time controlled to stop the etch at the correct depth or level so that the diaphragm remains and is the proper thickness. Other techniques will be evident to those of ordinary skill, e.g., deposition of a protective layer, e.g., silicon dioxide, on the top surface followed by the directional etch through the top layer from the back side to the protective layer and that followed by a further deposition on the top surface over the protective layer.

If the pressure sensor is built or assembled at a nominal atmospheric pressure level that level will be the reference pressure in the cavity 113. Changes in pressure (shown as arrows 117) incident on the diaphragm 115, available via the port 112, will physically deform the diaphragm which in turn will deform piezo resistive transducers (PRTs) 119, 121 or piezo resistors (one shown as part of the pressure sensor 103 and another as part of the humidity sensor 107). The PRTs are formed from a material with piezo resistive properties, such as silicon, specifically p-doped silicon, where a physical deformation results in a change in resistance in the case of PRTs or p-doped silicon. The PRTs are formed, typically, via a deposition process as is known. The PRTs are normally placed in a position relative to the diaphragm such that deformation of the diaphragm also results in a desired deformation or change in physical dimensions or properties of the PRTs. Thus as illustrated, the PRTs may be disposed such that a portion of the PRT overlaps the corresponding cavity, i.e., PRT 119 overlaps cavity 113. The pressure sensor, by virtue of the PRTs as further discussed below, will sense deformation of the diaphragm and associated PRTs and thus deviations from the nominal pressure and provide a corresponding signal or value related to pressure.

The humidity sensor 107 is generally comprised of a cavity 123, which may also be referred to as a pressure reference cavity although if the cavity is vented the pressure on both sides of the diaphragm is equal. Further included is a diaphragm 125 which, as above, is a thin layer (typically silicon layer of 6 microns or so). Similar to above this reference cavity 123 can be formed in the upper or top layer 111 via a directional or anisotropic etch with the etch time controlled to stop the etch at the correct depth or level so that the diaphragm remains and is the proper thickness. It will be appreciated that both diaphragms can be formed at the same time using the same processes. As above, other techniques will be evident to those of ordinary skill.

Further included in the humidity sensor is a humidity or water sensitive layer or film 127 disposed on the upper layer 111 over at least a portion of the humidity sensor diaphragm 125. The humidity sensitive layer or film 127 can be formed from a polyimide film. Those or ordinary skill will appreciate that polyimide films can be formed from various products including possibly a photo resist material. As will be appreciated by those of ordinary skill, the water sensitive layer 127 can be formed and disposed in the appropriate location with appropriate dimensions via known semiconductor processes. Generally as this layer is exposed to and absorbs more or less moisture the film will expand or shrink. As the film expands the diaphragm will deform or bow upward and as the film shrinks the diaphragm will deform or cup downward. This deformation of the diaphragm will also deform associated PRTs 121 (one shown). The humidity sensor, by virtue of the PRTs as will be further discussed below, will sense deformation of the diaphragm and PRTs and thus deviations from the nominal humidity or changes in humidity and provide a corresponding signal or value.

The humidity sensor by virtue of the cavity 123 and diaphragm 125 is subjected to or can be subjected to pressure and changes in pressure and thus pressure effects as generally indicated by the arrows 129. The combination sensor may need to offset any of these pressure effects on the humidity sensor. In some embodiments the integrated circuit die and one or more of the humidity sensor and pressure sensor are arranged and configured to facilitate offsetting any pressure effects on the humidity sensor. In some embodiments, the integrated circuit die comprises a vent opening to equalize pressure effects on the humidity sensor. The vent opening can be provided in any manner (top, bottom, side, etc. of die or small opening in diaphragm 125) which provides the same pressure to each side of the diaphragm 125.

In some embodiments as shown, the integrated circuit die comprises a vent opening 131 through a backside 133 or bottom surface of the integrated circuit die, where the vent opening is disposed, e.g., so as to at least partially join the cavity 123 and lie beneath the diaphragm 125 and thus so as to equalize pressure effects on the humidity sensor. In other embodiments given that the humidity sensor is provided in combination with the pressure sensor, the vent opening and process costs associated with providing the opening need not be incurred. In these embodiments, values from the pressure sensor can be used to offset the pressure effects on values from the humidity sensor. For example in some embodiments the values from the pressure sensor or corresponding values or some portion of those values can be subtracted from the values from the humidity sensor to offset the pressure effects on the values from the humidity sensor.

Figure 2:
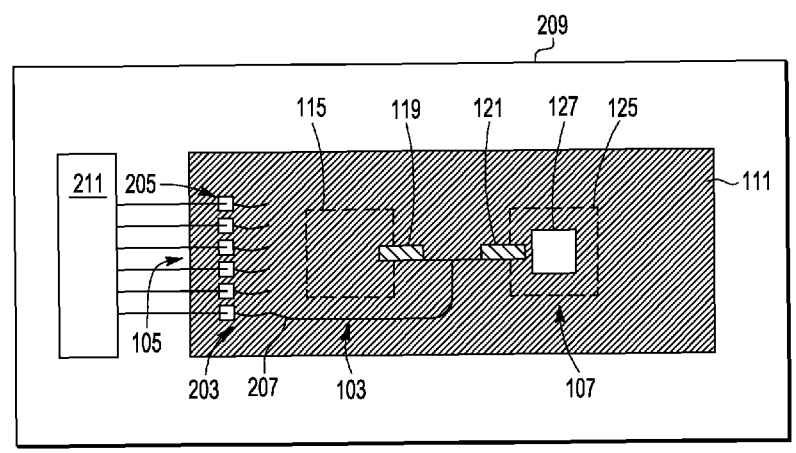
FIG. 2 in a representative form, shows a top view diagram of the combination sensor of FIG. 1 in accordance with one or more embodiments

Referring to FIG. 2, in a representative form, a top view diagram of the combination sensor of FIG. 1 in accordance with one or more embodiments will be briefly discussed and described. FIG. 2 shows the combination sensor 101 in a top plan view including the pressure sensor 103 with diaphragm 115 disposed on the die or integrated circuit die 105. Thus in some embodiments the combination sensor includes a diaphragm associated with the pressure sensor and a second diaphragm associated with the humidity sensor. Further illustrated is the humidity sensor 107 with diaphragm 125 disposed on the integrated circuit die 105 as well as a circuit 203 (108 is part of the circuit) which is coupled to, specifically PRTs 119, 121, and shared by the pressure sensor and the humidity sensor to facilitate pressure and humidity sensing. The circuit in various embodiments, further comprises bond pads 205 and traces 207 (not all bond pads or traces are shown for various embodiments) that provide, e.g., common bias voltages, etc. to the pressure sensor and the humidity sensor. As shown, some embodiments can include as a separate integrated circuit 211 or possibly, additional electronics and circuitry integrated with the combination sensor integrated circuit die, which circuits or electronics can convert the values from the pressure sensor and the humidity sensor into pressure and humidity readings. The circuit and interconnections and further details regarding the pressure sensor and humidity sensor will be discussed below with reference to FIG. 3. Also illustrated in a representative form is a common package 209 (similar to 109) enclosing the combination sensor and circuit 211.

While only one PRT is shown for each of the pressure and humidity sensors, some embodiments include additional PRTs. In some embodiments, the pressure sensor is further comprised of one or more piezo resistive transducers and the humidity sensor is further comprised of another one or more piezo resistive transducers. As will be illustrated and discussed below with reference to FIG. 3, at least one of the one or more and the another one or more piezo resistive transducers is comprised of a plurality of piezo resistive transducers arranged in a Wheatstone bridge configuration. In these embodiments one, two, three, or four piezo resistive transducers can be in the Wheatstone bridge configuration. Thus in some embodiments the plurality of piezo resistive transducers is further comprised of four piezo resistive transducers arranged in the Wheatstone bridge configuration.

Figure 3:
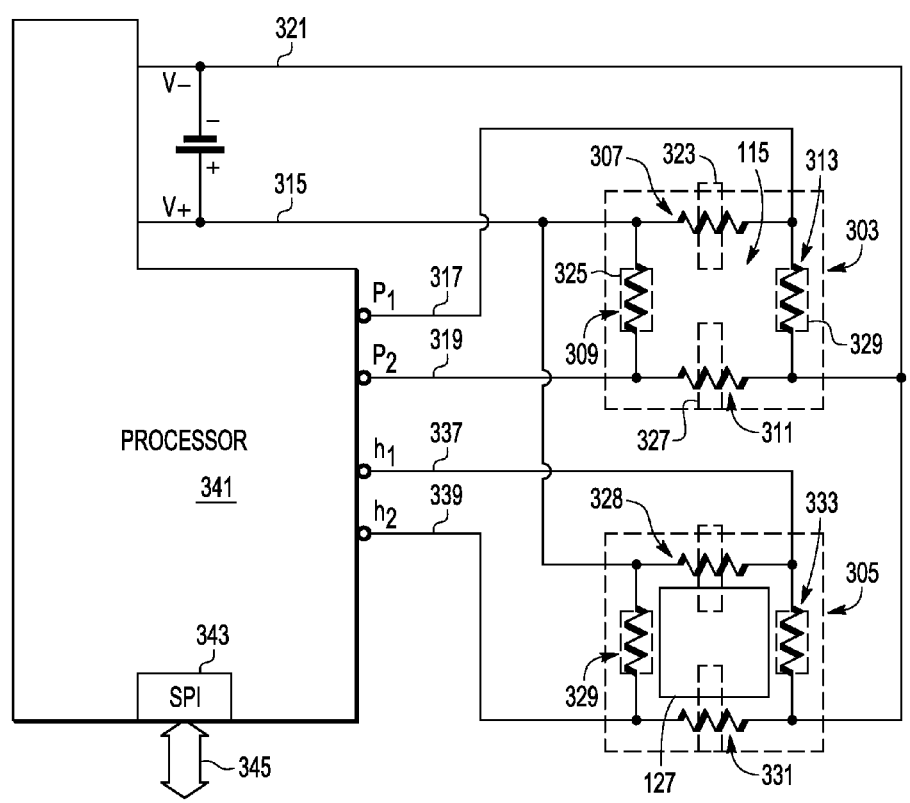
FIG. 3 depicts a representative schematic diagram of an exemplary combination sensor in accordance with one or more embodiments.

Referring to FIG. 3, a representative schematic diagram of an exemplary combination sensor, such as the sensor shown in FIG. 1 and FIG. 2, in accordance with one or more embodiments will be briefly discussed and described. FIG. 3 shows a Wheatstone bridge configuration 303 (dotted line enclosure) which is arranged and configured to facilitate pressure measurements, i.e. is a portion of the pressure sensor 103. Further illustrated is another Wheatstone bridge configuration 305 (dotted line enclosure) which is arranged and configured to facilitate humidity measurements, i.e. is a portion of the humidity sensor 107.

In various embodiments, the pressure sensor is comprised of one or more piezo resistive transducers and the humidity sensor is also comprised of one or more piezo resistive transducers. More specifically the pressure sensor includes PRTs 307, 309, 311, 313 (shown as piezo resistors) are coupled end to end (via traces on the die) to form four junctions, nodes or corners as shown. PRT 307 is coupled to PRT 309 at one node or corner 315 which can be connected to a bias voltage V+ or a positive supply voltage. PRT 307 is also series coupled to PRT 313 at another node P1 (pressure node 1) 317. PRT 309 is also series coupled to PRT 311 at another node P2 (pressure node 2) 319. PRT 311 is then coupled to PRT 313 at a further node or corner 321 which can be connected to a bias voltage V− or the negative supply voltage. Thus PRTs 307, 309, 311, 313 as connected are arranged and constructed to form the Wheatstone bridge configuration 303.

The PRTs while shown symbolically as resistors are actually silicon areas shown in a representative manner as small boxes or rectangles under each resistor symbol. On the die, these small boxes are areas where p-doped silicon or the like has been deposited via known processes and the connections illustrated schematically would be traces interconnecting the PRTs and bonding pads, etc. Thus PRT 307 is the silicon area 323, PRT 309 is the silicon area 325, PRT 311 is the silicon area 327, and PRT 313 is the silicon area 329. These silicon areas are shown as boxes or rectangles and each have a length (top to bottom) and width (side to side). As is known the resistance of each of these rectangles is proportional to the length divided by the width of the respective rectangle. While not specifically shown, in many embodiments, the perimeter of the cavity, i.e., reference cavity 113, which is underlying the rectangles can pass essentially through the middle of the length wise dimension of each respective resistor symbol, i.e. through the width dimension of silicon areas 323, 327 and through the length dimension of silicon areas 325, 329. There are many configurations and dispositions of the PRTs with respect to the cavity and these may vary with application and technology.

If a force is applied to the top of the diaphragm 115, it will be deformed in a direction opposite to the force, i.e., downward or inward, and silicon areas 323, 327 while deforming would increase in length while silicon areas 325, 329 would increase in width. This means that PRT 307, 311 will increase in resistance and PRT 309, 313 will decrease in resistance. This opposite change in resistance together with the Wheatstone bridge configuration will enhance any change between P1 317 and P2 319, where if all resistors are nominally equal the enhancement would be a doubling in incremental signal. The difference between the voltage at P1 and P2 is the value that is provided by the pressure sensor and this value will be proportional to the pressure that is applied to the diaphragm.

As noted earlier, the humidity sensor in various embodiments is also comprised of one or more piezo resistive transducers. More specifically the humidity sensor includes PRTs 328, 329, 331, 333 (shown as piezo resistors) are coupled end to end to form four junctions, nodes or corners as shown. PRT 317 is coupled to PRT 319 at one node or corner 315 which can be connected to a bias voltage V+ or a positive supply voltage. PRT 328 is also series coupled to PRT 333 at another node h1 (humidity node 1) 337. PRT 329 is also series coupled to PRT 331 at another node h2 (humidity node 2) 339. PRT 331 is then coupled to PRT 333 at a further node or corner 321 which can be connected to a bias voltage V− or the negative supply voltage. Thus PRTs 328, 329, 331, 333 as connected are arranged and constructed to form the Wheatstone bridge configuration 305.

The PRTs, as above, while shown symbolically as resistors are actually silicon areas shown in a representative manner as small boxes or rectangles under each resistor symbol. These silicon areas are shown as boxes or rectangles and each have a length (top to bottom) and width (side to side). As is known the resistance of each of these rectangles is proportional to the length divided by the width of the respective rectangle. While not specifically shown, in many embodiments, the perimeter of the cavity, i.e., reference cavity 123, which is underlying the rectangles can pass essentially through the middle of the length wise dimension of each respective resistor symbol. As above, there are many configurations and dispositions of the PRTs with respect to the cavity and these may vary with application and technology.

Further shown is the water or humidity sensitive layer 127 which will expand/contract as more/less moisture is absorbed. Contraction is the equivalent of a downward force and expansion is equivalent of less force. If a force is applied to the top of the diaphragm 125 (diaphragm underlying layer 127 but not specifically shown), contraction do to lower humidity, it will be deformed in a downward or inward direction and silicon areas along the upper and lower boundaries while deforming would increase in length while silicon areas along the sides would increase in width. This means that PRTs at the top and bottom will increase in resistance and PRTs along the sides will decrease in resistance. This opposite change in resistance together with the Wheatstone bridge configuration will enhance any change between h1 337 and h2 339, where if all resistors are nominally equal the enhancement would be a doubling in incremental signal. The difference between the voltage at h1 and h2 is the value that is provided by the pressure sensor and this value will be proportional to the deformation of the diaphragm as a result of expansion or shrinkage of the humidity sensitive layer.

Thus as shown and discussed, certain embodiments of the combination sensor include a pressure sensor or a humidity sensor, each with as many as four piezo resistive transducers arranged in the Wheatstone bridge configuration wherein the Wheatstone bridge further comprises first and second traces (at node 315, and node 321 for coupling bias voltages, V+, V−, to opposite corners of the Wheatstone bridge configuration and sensing traces (at nodes P1, P2 317, 319 for pressure values or h1, h2 337, 339 for humidity values) for coupling sensing signals from the other or alternate opposite corners of the Wheatstone bridge configuration.

Further generally shown in FIG. 3 is a processor 341 or controller which may be a simple application specific integrated circuit together with some memory for firmware, a look up table, regression parameters or the like. This processor may be a separate integrated circuit that is included and packaged with the pressure and humidity sensor and circuitry on a common carrier (not specifically shown) or provided in a separate package as desired by the end user. The task or functions of the processor, when the processor is provided include, e.g., to translate the signals or values provided by the pressure sensor at nodes 317, 319 and the values or signals provided by the humidity sensor at nodes 337, 339 into data or pressure and humidity readings or parameters at output 345 in a form desired by an end user. This task includes, e.g., converting values to parametric relevant results, e.g., 1.4 volts is equivalent to xyz millibars of atmospheric pressure or ab % relative humidity and also possibly converting the data form, e.g., an analog signal or value from the sensors to a possibly digital value or word and doing so such that the value is provided when required.

For example, if a serial peripheral interface (SPI) 343 is provided, serial data would be available as requested and this data could be in a specific form, i.e., order, resolution, etc. The SPI is a well known interface that includes clock, data I/O and chip select lines. Furthermore, when a combination sensor is manufactured, the device can be calibrated, known pressure levels or humidity levels applied with results recorded and the processor 341 loaded or programmed with the relevant information (look up table information or regression curve constants or the like) that allows for providing accurate parametric results and possibly programming output parameter data forms, e.g., digital 16 bit words, etc.

Figure 4:
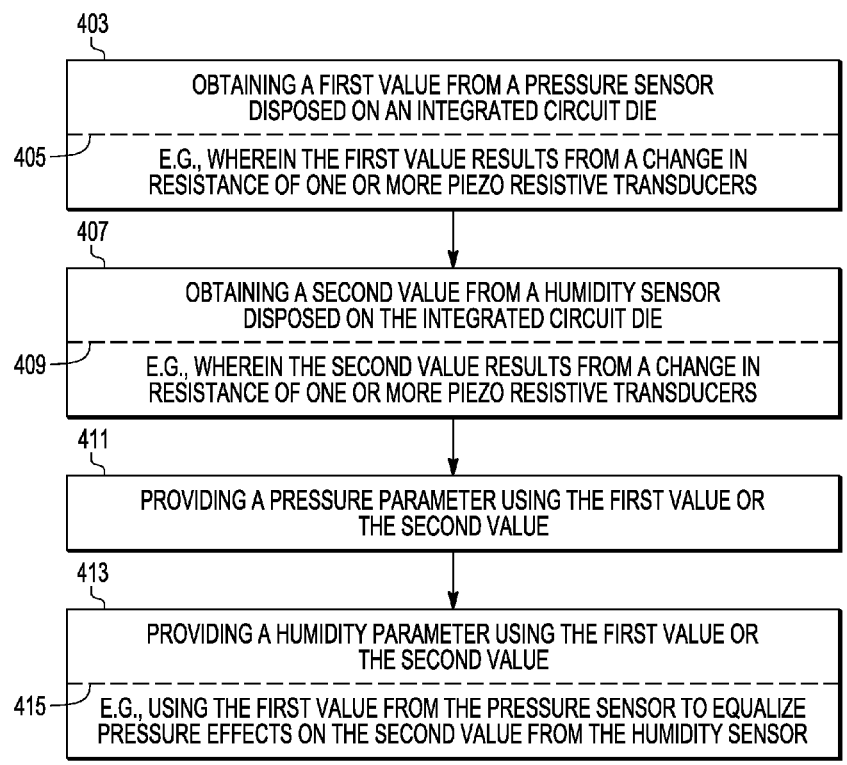
FIG. 4 shows a flow chart of processes executed by a method of measuring environmental parameters that may be used in conjunction with the FIG. 1 sensor in accordance with one or more embodiments.

Referring to FIG. 4, a flow chart of exemplary processes executed by methods of measuring environmental parameters that may be used in conjunction with the FIGS. 1, 2, and 3 structures in accordance with one or more embodiments will be discussed and described. It will be appreciated that this method uses many of the inventive concepts and principles discussed in detail above and thus this description will be somewhat in the nature of a summary with various details generally available in the earlier descriptions. This method can be implemented in one or more of the structures or apparatus described earlier or other similarly configured and arranged structures. It will be appreciated that the method can be performed in total or in part as many times as desired or continually performed as needed and one may begin or end at any particular part of the flow charts.

As indicated FIG. 4 shows a flow chart for methods of measuring a plurality of environmental parameters, where one or more such methods include obtaining 403 a first value corresponding to pressure from a pressure sensor disposed on an integrated circuit die, ceramic carrier or other suitable carrier. The pressure sensor in various embodiments as noted above can include a diaphragm for a diaphragm based pressure sensor or other suitable arrangements or structures for assessing environmental pressures. The obtaining 403 a first value in some embodiments further comprises obtaining, e.g., 407 a first value resulting from a change in resistance of one or more piezo resistive transducers (PRTs) disposed on the integrated circuit die with the one or more PRTs (with each PRT including as many piezo resistors as desired) possibly arranged in part or total in a Wheatstone bridge configuration.

Further included is obtaining 407 a second value corresponding to humidity from a humidity sensor disposed on the integrated circuit die. The humidity sensor can include a diaphragm or a cantilever beam or any other structure that facilitates assessing environmental humidity. The obtaining a first value related to humidity can, in some embodiments, further comprise obtaining, e.g., 409 a second value resulting from a change in resistance of another one or more piezo resistive transducers (PRTs) disposed on the integrated circuit die with the one or more PRTs (with each PRT including as many piezo resistors as desired) possibly in a Wheatstone bridge configuration. The combination sensor and specifically the pressure and humidity sensors can be enclosed or encased in a sensor package suitable for there respective purposes.

Additionally included is providing 411 a pressure parameter (actual pressure reading or measurement) using at least one of the first value associated with pressure and possibly the second value associated with humidity. Further, illustrated is providing 413 a humidity parameter (actual humidity reading or measurement) using at least one of the first value associated with pressure and the second value associated with humidity. In some embodiments, the integrated circuit die further comprises a vent opening (backside or otherwise) to equalize pressure effects on the second diaphragm for the humidity sensor. Some embodiments can further include, e.g., using 415 the first value from the pressure sensor to equalize pressure effects on the second value from the humidity sensor. By knowing the pressure effects these can be eliminated from the humidity sensor values, e.g., by subtracting all or a portion of the first value obtained from the pressure sensor from those values obtained from the humidity sensor.

The processes, apparatus, and systems, discussed above, and the inventive principles thereof are intended to and can alleviate various economic cost and quality issues by reducing or eliminating extra physical space, duplicated inputs/outputs, duplicated power distribution, duplicated bonding pads and wires, etc. caused by or resulting from prior art techniques of having separate sensors and attendant problems. Using the principles of combining sensors given an assumption that similar process technologies are used can result in nearly identical sensor characteristics in terms of diaphragm and PRT characteristics and can quickly yield an accurate combination sensor with significant possible cost savings and other efficiencies.

This disclosure is intended to explain how to fashion and use various embodiments in accordance with the invention rather than to limit the true, intended, and fair scope and spirit thereof. The foregoing description is not intended to be exhaustive or to limit the invention to the precise form disclosed. Modifications or variations are possible in light of the above teachings. The embodiment(s) was chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled.

What is claimed is:

1. A combination sensor comprising:
   a pressure sensor disposed on a die, the die including a semiconductor material, wherein the pressure sensor is comprised of four piezo resistive transducers arranged in a first Wheatstone bridge configuration;
   a humidity sensor disposed on the die, wherein the humidity sensor is comprised of another four piezo resistive transducers arranged in a second Wheatstone bridge configuration; and
   a circuitry disposed on the die and coupled to and shared by the pressure sensor and the humidity sensor to facilitate pressure and humidity sensing,
   wherein the circuitry comprises one or more bond pads and traces that provide one or more common bias voltages to both the pressure sensor and the humidity sensor, and the circuitry further comprises first and second traces on the die for coupling the bias voltages to opposite corners of the first Wheatstone bridge configuration and the second Wheatstone bridge configuration and pressure sensing traces for coupling pressure sensing signals from the other opposite corners of the first Wheatstone bridge configuration and humidity sensing traces for coupling humidity sensing signals from the other opposite corners of the second Wheatstone bridge configuration.

2. The combination sensor of claim 1 further comprising a sensor package encasing the pressure sensor and the humidity sensor.

3. The combination sensor of claim 1 wherein the die further comprises a first diaphragm associated with the pressure sensor and a second diaphragm associated with the humidity sensor.

4. The combination sensor of claim 3 wherein the first diaphragm and the second diaphragm are formed on a same layer of the die.

5. A combination sensor comprising:
   a pressure sensor disposed on a die, the die including a semiconductor material;
   a humidity sensor disposed on the die, wherein the die comprises a vent opening to equalize pressure effects on the humidity sensor; and
   a circuitry disposed on the die and coupled to and shared by the pressure sensor and the humidity sensor to facilitate pressure and humidity sensing,
   wherein the die and one or more of the humidity sensor and pressure sensor are arranged and configured to facilitate offsetting any pressure effects on the humidity sensor.

6. The combination sensor of claim 5 wherein the vent opening is through a backside of the die.

7. The combination sensor of claim 5 wherein values from the pressure sensor are used to offset the pressure effects on values from the humidity sensor.

8. The combination sensor of claim 7 wherein a portion of the values from the pressure sensor are subtracted from the values from the humidity sensor to offset the pressure effects on values from the humidity sensor.

9. A method of measuring a plurality of environmental parameters, the method comprising:
   obtaining a first value corresponding to pressure from a pressure sensor disposed on a die;
   obtaining a second value corresponding to humidity from a humidity sensor disposed on the die, wherein the die comprises a vent opening to equalize pressure effects on a diaphragm for the humidity sensor;
   providing a pressure parameter using at least one of the first value and the second value; and
   providing a humidity parameter using at least one of the first value and the second value,
   wherein any pressure effects on the humidity sensor are equalized.

10. The method of claim 9 wherein the die is encased in a sensor package.

11. The method of claim 9 wherein the pressure sensor is comprised of a first diaphragm, the diaphragm for the humidity sensor is a second diaphragm, and the first and second diaphragms are formed on the same layer of the die.

12. The method of claim 9 further comprising using the first value from the pressure sensor to equalize pressure effects on the second value from the humidity sensor.

13. The method of claim 9 wherein the obtaining a first value further comprises obtaining a first value resulting from a change in resistance of one or more piezo resistive transducers included with the pressure sensor and wherein the obtaining second value further comprises obtaining a second value resulting from a change in resistance of another one or more piezo resistive transducers included with the humidity sensor.

14. The method of claim 13 wherein the one or more piezo resistive transducers comprises a plurality of piezo resistive transducers arranged in a first Wheatstone bridge configuration and the another one or more piezo resistive transducers comprises a plurality of piezo resistive transducers arranged in a second Wheatstone bridge configuration and wherein one or more bond pads are used to couple one or more common bias voltages to the first and second Wheatstone bridge.

* * * * *